US00PP23739P3

(12) United States Plant Patent
Bradford

(10) Patent No.: US PP23,739 P3
(45) Date of Patent: Jul. 16, 2013

(54) INTERSPECIFIC TREE NAMED 'BLACK MAJESTY IV'

(50) Latin Name: *Prunus sp.*
Varietal Denomination: Black Majesty IV

(76) Inventor: Lowell Glen Bradford, Le Grand, CA (US)

( * ) Notice: Subject to any disclaimer, the term of this patent is extended or adjusted under 35 U.S.C. 154(b) by 77 days.

(21) Appl. No.: 13/374,024

(22) Filed: Dec. 8, 2011

(65) Prior Publication Data

US 2013/0152246 P1 Jun. 13, 2013

(51) Int. Cl.
*A01H 5/00* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP15,809 P2 6/2005 Bradford
PP18,668 P2 3/2008 Bradford

*Primary Examiner* — Annette Para

(57) ABSTRACT

The present invention relates to a interspecific tree and more particularly to a new and distinct variety broadly characterized by a medium size, moderately vigorous, hardy, and productive tree. Being self-unfruitful, the present variety requires cross pollination from an apricot, interspecific, or plum that blooms during the mid to late season. The present variety produces a very heavy bloom with a moderate amount of pollen to entice good bee activity to facilitate pollination. The fruit matures under the ecological conditions described during the latter half of July, with first picking on Jul. 23, 2011. The fruit is uniformly large in size, blackish red in skin color, clingstone in type, fairly globose in shape, orange to yellow in flesh color, firm in texture, and sweet in flavor.

1 Drawing Sheet

Botanical classification: *Prunus* sp.
Varietal denomination: 'BLACK MAJESTY IV'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Black Majesty IV'.

During a typical blooming season I isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2000 one such house containing 'Yummygem' (U.S. Plant Pat. No. 15,809) plum was crossed by me in this manner. To pollinate this plum, I selected bouquets from several sources of apricot and interspecific hybrid trees without keeping specific written details. Upon reaching maturity the fruit from this plum tree was harvested and the seeds were removed, cracked, stratified and germinated as a group with the label "10P881". They were grown as seedlings on their own root in my greenhouse and upon reaching dormancy transplanted to a cultivated area of my experimental orchard located near Le Grand, Calif. in Merced County (San Joaquin Valley). During the spring of 2005 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was true to type.

The present variety is similar to its seed parent, 'Yummy®gem' plum (U.S. Plant Pat. No. 15,809), by being self-unfruitful and by producing fruit that is nearly black in skin color, mostly yellow in flesh color, firm in texture, and almost globose in shape, but is quite distinguished therefrom by producing fruit that is somewhat sweeter in flavor, much larger in size, and that matures about twenty-five days later.

The present variety is most similar to 'Blackred III' interspecific (U.S. Plant Pat. No. 18,668) by being self-unfruitful and by producing fruit that is nearly black in skin color, that is similar in size, that is juicy and firm, and that is sweet, but is distinguished therefrom by flowering much later and by producing fruit that is almost entirely yellow instead of pink in flesh color, and that matures about five days earlier.

SUMMARY OF VARIETY

The present interspecific variety is characterized by a medium size, moderately vigorous, hardy, and productive tree. Being self-unfruitful, the present variety requires cross pollination from an apricot, interspecific, or plum that blooms during the mid to late season. The present variety produces a very heavy bloom with a moderate amount of pollen to entice good bee activity to facilitate pollination. The fruit matures under the ecological conditions described during the latter half of July, with first picking on Jul. 23, 2011. The fruit is uniformly large in size, blackish red in skin color, clingstone in type, globose in shape, orange to yellow in flesh color, firm in texture, and sweet in flavor.

DRAWING

The accompanying photograph consists of four whole fruits positioned to display the characteristics of the skin color and form, a half fruit divided to reveal the flesh and stone, and typical leaves.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Jul. 28, 2011, on the original tree during its eleventh growing season. The flower and bud descriptions were developed during the previous blooming season. All major color code designations are by reference to the Inter-Society Color Council, National Bureau of Standards. Common color names are also used occasionally.

PARENTAGE

Seed parent: 'YUMMY® GEM' (U.S. Plant Pat. No. 15,809).
Pollen parent: Unknown.

TREE

Size: Medium, reaching and maintaining a height of 10' [3.05 m.] and a spread of 10' [3.05 m.] after eleven growing seasons utilizing typical dormant pruning.

Vigor: Medium vigor, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable mid to late seasonal blooming apricot, interspecific or plum, such as 'Plumsweet IV' (U.S. Plant Pat. No. 16,461) interspecific.

Bearing: Regular bearing observed thus far, weather dependent.

Trunk:

- *Size.*—Medium, reaching a maximum diameter of 5½" [139.7 mm.] after the eleventh growing season.
- *Texture.*—Shaggy.
- *Bark color.*—A Grayish brown [61. gy.Br] and Strong brown [55. s.Br] variegation.
- *Lenticels.*—Approximate Number Per Square Inch: 12. Color: Dark orange yellow [72. d.OY]. Size: ⅛" [3.2 mm.] to ⅜" [9.5 mm.]. Shape: Eye-shaped, elongated.

Branches:

- *Size.*—Diameter of the main scaffold is 3" [76.2 mm.] measured 12" above the crotch, diameter of the limb is 1⅝" [41.3 mm.] measured 12" above first fork.
- *Texture.*—Smooth on first and second year wood, increasing roughness with age.
- *Color.*—1st Year Wood Topside: Grayish red [19. gy.R]. 1st Year Wood Underside: Brilliant yellow green [116. brill.YG]. 2nd Year Wood: Strong brown [55. s.Br] with Strong yellow green [117. s.YG] permeating through from underneath. 3rd Year Wood: A Grayish brown [61. gy.Br] and Strong brown [55. s.Br] variegation.
- *Lenticels.*—Number Per Square Inch: About 70 on second year wood. Color: Light yellowish brown [76. l.yBr]. Size: 1/64" [0.4 mm.] to 1/16" [1.6 mm.]. Shape: Eye-shaped, elongated.

Leaves:

- *Size.*—Large. Average Length: 4¾" [120.7 mm.]. Average Width: 2 5/16" [58.8 mm.].
- *Arrangement.*—Alternate.
- *Thickness.*—Medium.
- *Form.*—Elliptical.
- *Apex.*—Acuminate.
- *Base.*—Acute with an average angle base angle of 75 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average Length: ½" [12.7 mm.]. Average Thickness: 1/16" [1.6 mm.]. Color: Brilliant yellow green [116. brill.YG] becoming Grayish brown [61. gy.Br] with age.
- *Stipules.*—Number: Usually 2 per leaf, up to 6 per growing tip. Average Length: ⅜" [9.5 mm.]. Color: Light yellow green [119. l.YG].
- *Glands.*—Number: 1 to 4 per leaf, mostly 2. Position: Alternately positioned at the intersection of the petiole and on the leaf blade. Size: Small. Form: Globose. Color: Light yellow green [119. l.YG] becoming Moderate brown [58. m.Br] in the center with age.
- *Leaf buds.*—Pointed, medium.

Flower buds:

- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Tip color.*—White [263. White] with Pale yellowish pink [31. p.yPk] on some.

Flowers: Perfect, complete, perigynous, usually a single pistil, typically thirty or more stamens, five sepals and petal locations alternately positioned.

- *Average flower diameter.*—1" [25.4 mm.].
- *Number of petals.*—Five, no double blossoms observed.
- *Petal shape.*—Oval to circular.
- *Petal margin.*—Entire, smooth to slightly wavy.
- *Average petal diameter.*—½" [12.7 mm.].
- *Average petal length.*—9/16" [14.3 mm.].
- *Petal apex.*—Rounded.

*Petal base.*—Obtuse.
*Petal color.*—White [263. White] on both sides.
*Anther color.*—Dark reddish orange [38. d.rO] over a Brilliant yellow [83. brill.Y] center.
*Stigma color.*—Light greenish yellow [101 l.gY].
*Sepal color.*—A Brilliant yellow green [116. brill.YG] and Grayish purplish Red [262. gy.pR] two-tone on the outer surface.
*Sepal length.*—3/16" [4.8 mm.].
*Sepal width.*—5/32" [4.0 mm.].
*Sepal apex.*—Rounded to elliptical to match the width and length.
*Sepal margin.*—Fairly smooth with slight serrations toward the apex.
*Average pistil length.*—5/8" [15.9 mm.].
*Average stamen length.*—7/16" [11.1 mm.].
*Fragrance.*—Moderate.
*Bloom density.*—Very heavy.
*Number per cluster.*—2 to 10, average 5.
*Pollen production.*—Medium, average enticement to bees.
*Blooming period.*—Mid to late, with 'September Yummy®' plum (U.S. Plant Pat. No. 14,220).
*Onset of bloom.*—One percent on Mar. 2, 2011.
*Date of full bloom.*—Mar. 10, 2011.
*Duration of bloom.*—One to two weeks, dependent on ambient temperature.

FRUIT

Maturity when described: Firm ripe, Jul. 28, 2011.
Date of first picking: Jul. 23, 2011.
Date of last picking: Aug. 8, 2011.
Size: Uniform, large.
*Average diameter axially.*—2 11/16" [68.3 mm.].
*Average diameter across cheek plane.*—2 7/16" [61.9 mm.].
*Average diameter across suture plane.*—2 3/4" [69.9 mm.].
*Typical weight.*—6.4 ounces [181 grams].
Form: Uniform, mostly globose, sometimes asymmetrical.
*Longitudinal section form.*—Oval.
*Transverse section through axial diameter.*—Circular.
Suture: An inconspicuous shallow trough extending from the base to the apex.
Ventral surface: Strongly rounded, slightly lipped toward the apex.
Lips: Slightly unequal.
Cavity: Flaring, suture showing on one side, stem indentations occur occasionally.
*Depth.*—7/16" [11.1 mm.].
*Breadth.*—1 7/16" [36.5 mm.].
Base: Truncate.
Apex: Rounded.
Pistil point: An inconspicuous Grayish reddish brown [46. gy.rBr] dot located at the end of the suture.
Stem: Medium.
*Average length.*—7/16" [11.1 mm.].
*Average width.*—3/32" [2.4 mm.].
Skin:
*Thickness.*—Medium.
*Surface.*—Smooth.
*Tenacity.*—Tenacious to the flesh.
*Astringency.*—Somewhat.
*Tendency to crack.*—Slight in wet season.
*Color.*—Blackish red [21. blackish R] with a minor amount of Grayish reddish brown [46. gy.rBr] freckling throughout.
*Bloom.*—Abundant.
Flesh:
*Color.*—A blend of Brilliant orange yellow [67. brill.OY] with some Brilliant yellow [83. brill.Y].
*Surface of pit cavity.*—Covered with Moderate yellow [87. m.Y] broken fibers when twisted away from the stone.
*Amygdalin.*—Moderate.
*Juice.*—Moderate, rich.
*Texture.*—Firm, meaty.
*Fibers.*—Few, fine, tender.
*Ripens.*—Slightly earlier toward the apex.
*Flavor.*—A nice blend of acid and sugar, typically 19 brix.
*Aroma.*—Slight.
*Eating quality.*—Good.

STONE

Type: Clingstone.
Form: Oval.
Hilum: Narrow to slightly oblong.
Base: Truncate.
Apex: Acuminate with a very short 1/16" [1.6 mm.] tip.
Sides: Equal.
Surface: Rough throughout with a groove on each side of the dorsal fin.
External color of stone: Moderate orange [53. m.O] when dry.
Pit wall color when cracked: Dark orange yellow [72. d.OY].
Cavity surface color: Brownish orange [54. brO].
Average pit wall thickness: 1/16" [1.6 mm.].
Average width: 11/16" [17.5 mm.].
Average length.—1 1/16" [27 mm.].
Average breadth.—3/8" [9.5 mm.].
Tendency to split: None.
Kernel:
*Form.*—Oval.
*Skin color.*—Light yellow [86. l.Y].
*Pellicle color.*—Dark grayish yellow [91. d.gy.Y].
*Vein color.*—Light orange yellow [70. l.OY].
*Taste.*—Bitter.
*Viable.*—Yes.
*Average width.*—7/16" [11.1 mm.].
*Average length.*—5/8" [15.9 mm.].
*Amygdalin.*—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific tree, substantially as illustrated and described, that is most similar to 'Blackred III' interspecific (U.S. Plant Pat. No. 18,668) by being self-unfruitful and by producing fruit that is nearly black in skin color, that is similar in size, that is juicy and firm, and that is sweet, but is distinguished therefrom by flowering much later and by producing fruit that is almost entirely yellow instead of pink in flesh color, and that matures about five days earlier.

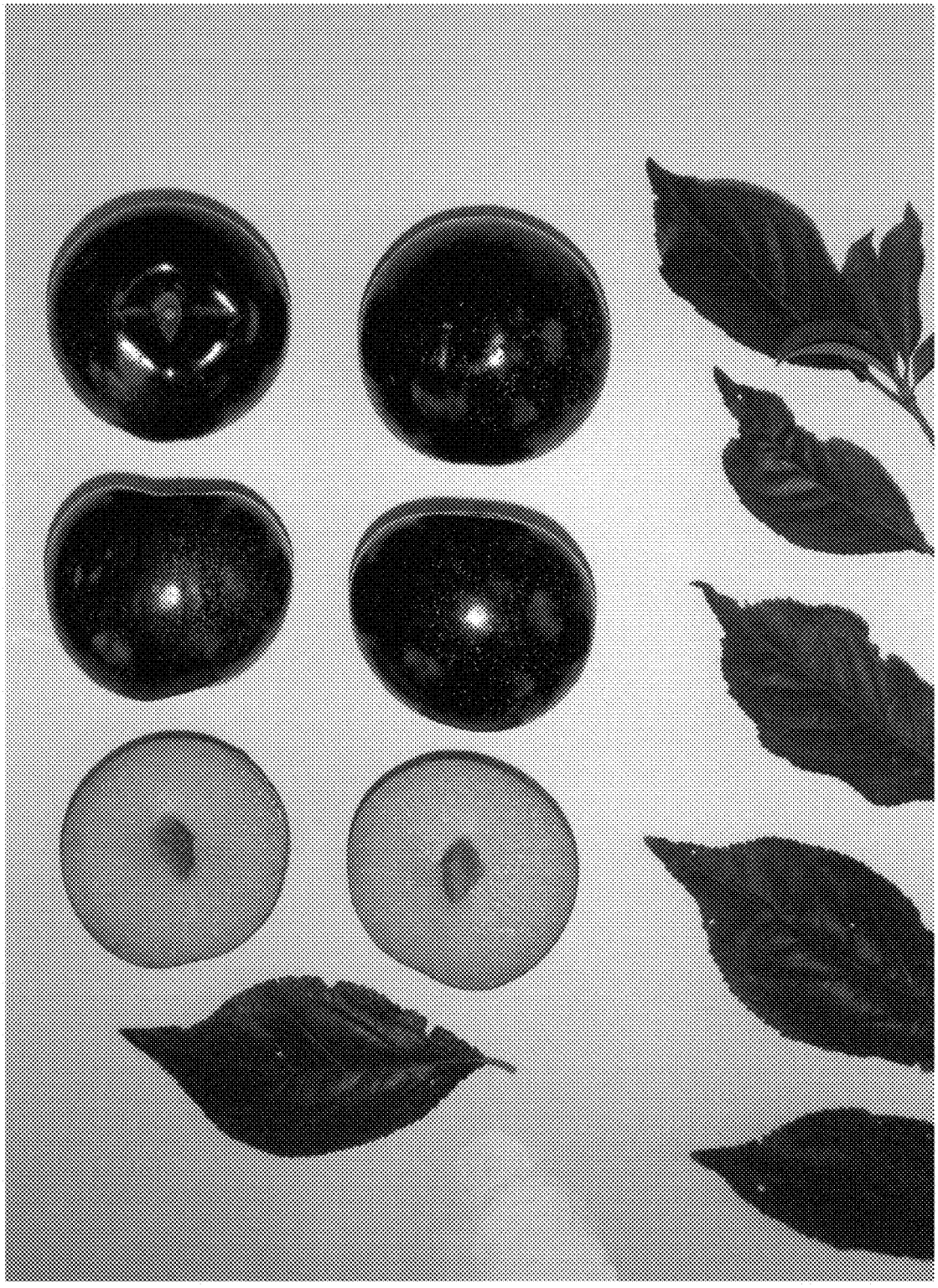

* * * * *